(12) United States Patent
Moskovich et al.

(10) Patent No.: US 8,387,197 B2
(45) Date of Patent: Mar. 5, 2013

(54) ORAL CARE IMPLEMENT HAVING AN ADJUSTABLE MASS CENTROID

(75) Inventors: Robert Moskovich, East Brunswick, NJ (US); Eduardo Jimenez, Manalapan, NJ (US)

(73) Assignee: Colgate-Palmolive Company, New York, NY (US)

( * ) Notice: Subject to any disclaimer, the term of this patent is extended or adjusted under 35 U.S.C. 154(b) by 1343 days.

(21) Appl. No.: 11/866,597

(22) Filed: Oct. 3, 2007

(65) Prior Publication Data

US 2009/0089950 A1    Apr. 9, 2009

(51) Int. Cl.
*A46B 5/00* (2006.01)
(52) U.S. Cl. .................. 15/143.1; 15/22.1; 15/167.1
(58) Field of Classification Search .............. 15/143.1, 15/144.1, 167.1, 159.1
See application file for complete search history.

(56) References Cited

U.S. PATENT DOCUMENTS

| | | | |
|---|---|---|---|
| 1,796,001 A | 4/1929 | Church | |
| 3,417,762 A * | 12/1968 | Hall | 401/176 |
| 4,253,212 A * | 3/1981 | Fujita | 15/167.1 |
| 4,680,825 A * | 7/1987 | White et al. | 15/105 |
| 4,787,765 A * | 11/1988 | Kuo | 401/191 |
| 5,134,743 A * | 8/1992 | Hukuba | 15/105 |
| 5,339,482 A | 8/1994 | Desimone et al. | |
| 5,524,312 A | 6/1996 | Tan et al. | |
| 5,572,763 A * | 11/1996 | Eguchi | 15/167.1 |
| 5,651,157 A * | 7/1997 | Hahn | 15/22.1 |
| 5,735,012 A | 4/1998 | Heinzelman et al. | |
| 5,956,796 A * | 9/1999 | Lodato | 15/167.1 |
| 6,213,663 B1 * | 4/2001 | Micaletti et al. | 401/176 |
| 6,298,516 B1 | 10/2001 | Beals et al. | |
| 6,353,958 B2 | 3/2002 | Weihrauch | |
| 6,568,020 B1 * | 5/2003 | Hosokawa | 15/22.1 |
| 6,685,375 B1 | 2/2004 | Crocker | |
| 7,047,591 B2 | 5/2006 | Hohlbein | |
| 2003/0056311 A1 * | 3/2003 | Broecker et al. | 15/167.1 |
| 2006/0195995 A1 | 9/2006 | Moskovich et al. | |
| 2007/0119010 A1 | 5/2007 | Hohlbein et al. | |

FOREIGN PATENT DOCUMENTS

| | | |
|---|---|---|
| EP | 0 303 385 A | 2/1989 |
| JP | 2002272536 A | 9/2002 |
| WO | WO 01/43580 | 6/2001 |
| WO | 2004028292 A | 4/2004 |
| WO | WO 2006/015196 | 2/2006 |

OTHER PUBLICATIONS

International Search Report PCT/US2008/078226 mailed Feb. 12, 2009.
Official Decision of Grant from the Patent Office of the Russian Federation, dated Apr. 7, 2011, for corresponding Russian Patent Application No. 2010117516.

* cited by examiner

*Primary Examiner* — Monica Carter
*Assistant Examiner* — Stephanie N Berry

(57) ABSTRACT

An oral care implement or toothbrush includes a head and a tooth cleaning element. The oral care implement's mass centroid may be adjusted to guard against the application of excessive force against a user's teeth. Adjustment may be performed using a variety of systems and mechanisms including adjustment of a weight within a portion of the oral care implement. The location of the weight may be modified using a variety of techniques including a screw configuration and/or a slider control.

7 Claims, 2 Drawing Sheets

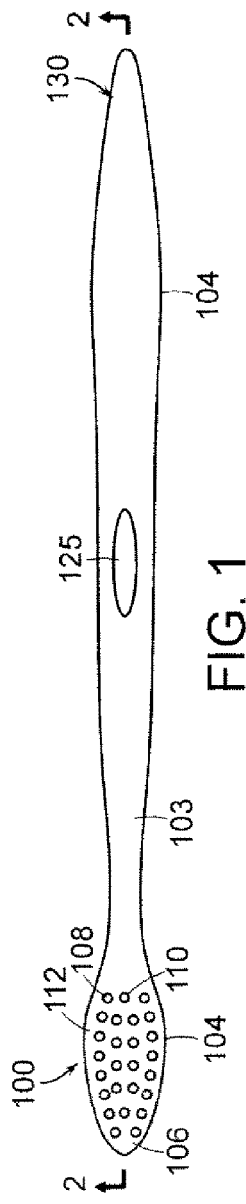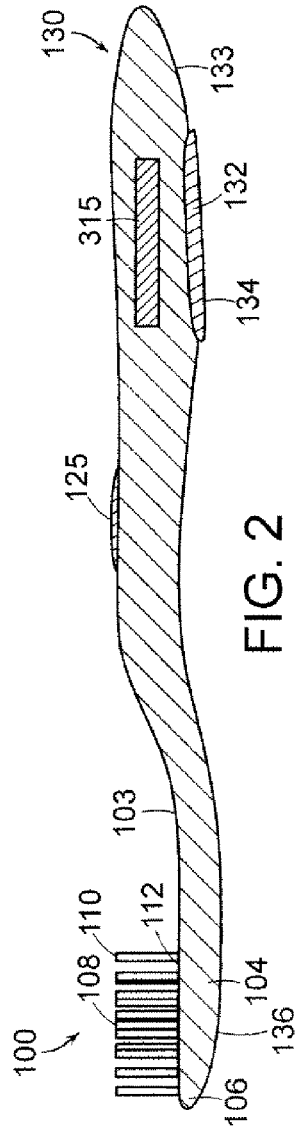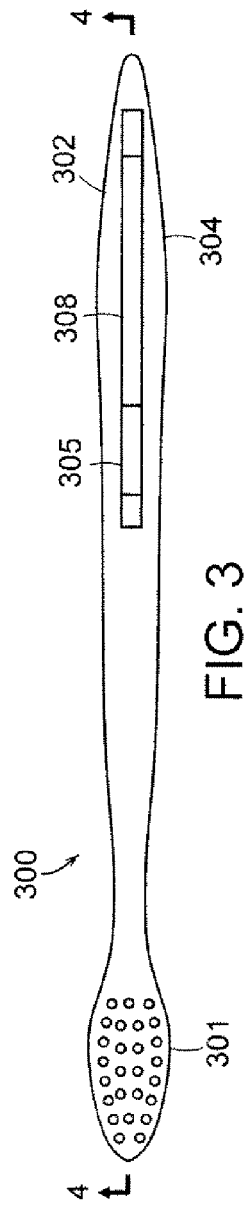

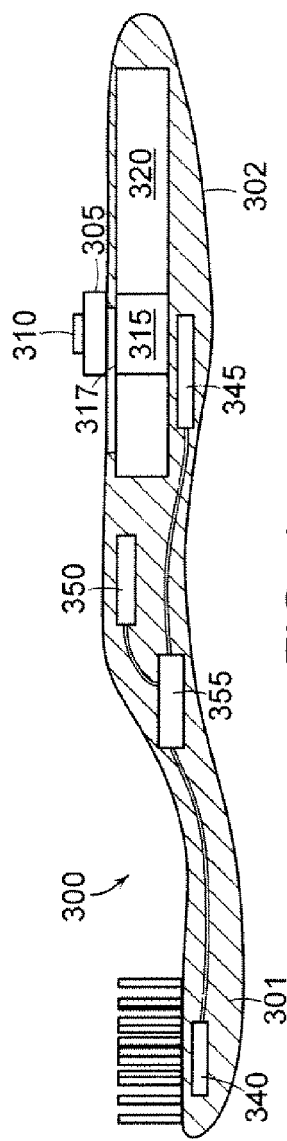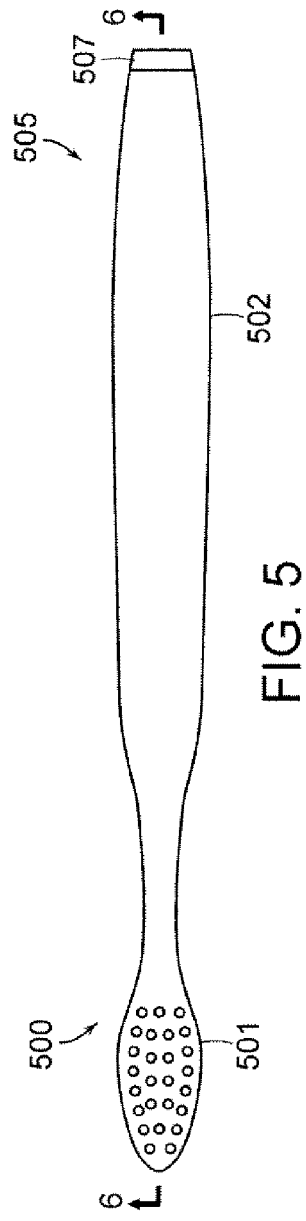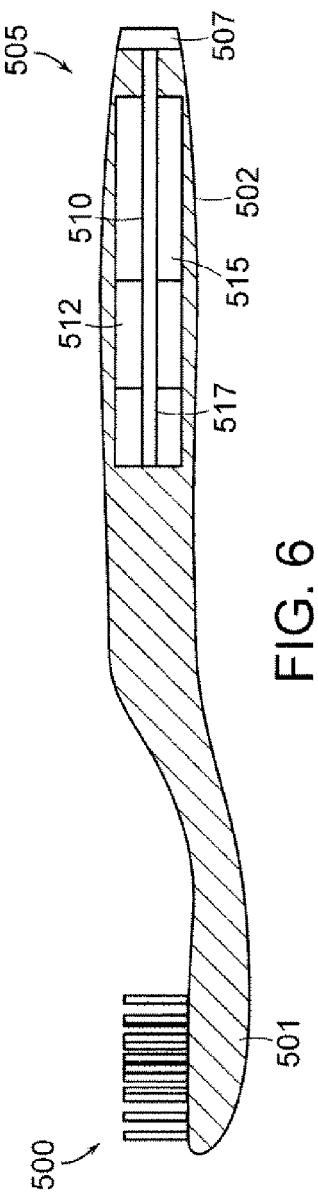

8,387,197 B2

ORAL CARE IMPLEMENT HAVING AN ADJUSTABLE MASS CENTROID

FIELD OF THE INVENTION

This invention relates generally to an oral care instrument, and, more particularly, to an oral care instrument having an adjustable mass centroid.

BACKGROUND OF THE INVENTION

A toothbrush is used to clean teeth by removing plaque and debris from surfaces of the teeth as well to clean gum tissue surrounding teeth. Conventional toothbrushes typically have a head having tufts of bristles, and may also have other types of cleaning structures. While toothbrushes according to the prior art provide a number of advantageous features, they nevertheless have certain limitations. For example, certain toothbrushes often do not prevent a user from applying too much force to their teeth. Thus, a user may be scraping off the enamel of his or her teeth while brushing. This may have adverse effects on the user's dental health. In some instances, the distribution of weight of a toothbrush may actually encourage or aid in the application of excessive force.

SUMMARY

The invention pertains to an oral care implement or toothbrush with a method and system for adjusting the mass centroid thereof.

According to one or more aspects, a mass centroid (or center of mass) of an oral care implement may be adjusted to counteract excessive force used in contacting a user's teeth with the head of the oral care implement. Generally, the mass centroid may be positioned past the point at which a user grips the oral care implement and opposite the teeth-contacting end. Providing a method and system for adjusting a mass centroid allows a user to grip the oral care implement at a desired location (i.e., rather than at a predefined location along the implement). The mass centroid may be adjusted to provide a sufficient counterforce based on the grip location. Various adjustment mechanisms and systems may be used including, for example, screw configurations and slider controls.

Other features and advantages of the invention will become apparent from the following description taken in conjunction with the following drawings.

BRIEF DESCRIPTION OF THE DRAWINGS

FIG. 1 is a front view of a toothbrush according to one or more aspects of an illustrative embodiment.

FIG. 2 is a cross-sectional view of the toothbrush of FIG. 1 along line 2-2.

FIG. 3 is a front view of a toothbrush having an adjustable mass centroid according to one or more aspects described herein.

FIG. 4 is a cross-sectional view of the toothbrush of FIG. 3 taken along line 4-4.

FIG. 5 is a front view of a toothbrush having a centroid adjustment mechanism according to one or more aspects described herein.

FIG. 6 is a cross-sectional view of a toothbrush of FIG. 5 taken along line 6-6 according to one or more aspects described herein.

DETAILED DESCRIPTION OF CERTAIN PREFERRED EMBODIMENTS

In the following description, the invention is discussed in terms of a toothbrush, but could be in the form of other oral care implements including simply a tissue cleansing implement. Further, it is understood that other embodiments may be utilized and structural and functional modifications may be made without departing from the scope of the present invention.

FIGS. 1-6 illustrate oral care implements, or toothbrushes, such as toothbrush 100 of FIG. 1. Toothbrush 100 generally includes a handle 102 and a head 104. Additionally, a longitudinal axis L may be defined as the axis running lengthwise from a bristle head, e.g., head 104, to a tail end 130 of handle 102. While aspects of various embodiments are described with respect to a toothbrush, the aspects described herein may be used with a variety of oral care implements such as interproximal picks, flossing tools, plaque scrapers, tongue and soft tissue cleansers/massagers and the like.

The handle 102 is generally an elongated member that is dimensioned for the user to readily grip and manipulate toothbrush 100. The handle 102 may be formed of many different shapes, lengths and with a variety of constructions. The handle 102 may have a neck portion 103 directly adjacent to the head 104. In one construction, the handle 102 is integrally formed with the head 104 although other attachment configurations are possible. Handle 102 may include a grip region having a grip element 125 that may, in one or more instances, comprise a non-slip (e.g., rubber) material to enhance a user's grip. Various types of grip materials and elements may also be used to provide tactile indication or grip enhancement.

The head 104 generally includes a support member 106, a first tooth cleaning element 108, and a second tooth cleaning element 110, which protrude outwardly from a front first surface 112 of head 104. The support member 106 is typically integrally formed with the handle 102 and supports the tooth cleaning elements 108, 110. The tooth cleaning elements 108 and 110 may be considered to be connected to the head 104. In one embodiment, the first tooth cleaning element 108 is formed from one or more bristles. Bristles may be in the form of tufts of bristles wherein the bristles may have the same or different diameters. Other configurations of the bristles are also possible. It is understood that the respective lengths of the first tooth cleaning element 108 and the second tooth cleaning element 110 can both independently vary as desired. The tooth cleaning elements 108, 110 can be attached to the support member 106 by known methods, such as being fit within recesses formed in the support member 106.

It is understood that the bristles (e.g., cleaning elements 108 and 110) may be made from nylon although a variety of other materials could be used in place thereof or in combination therewith. The bristles also preferably have a generally circular cross-sectional shape, but could have other cross-sectional shapes as well. The diameter of the bristles can vary depending on the desired cleaning action of the bristles.

Additionally, a mass centroid of toothbrush 100, or other oral care implement, may be defined as the center of mass of the toothbrush or other oral care implement. In one or more configurations, the mass centroid may be positioned such that a larger portion of toothbrush 100's weight is located toward tail end 130 of toothbrush 100 and past grip element 125. Positioning the mass centroid in such a manner (i.e., toward the tail end 130 and past grip element 125) may help counteract the application of excessive force when brushing one's teeth. While some pressure is desired to remove plaque and other unwanted particles, applying too much force against one's teeth may cause destruction and deterioration of enamel. In such configurations, grip element 125 may represent a pivot point where the mass centroid counteracts the force being applied through head 104.

In certain embodiments, a stabilizing element 132 may be provided on a rear surface 133 of handle 102. Stabilizing element 132 has a surface area 134. Surface area 134 may be substantially flat. Stabilizing element 132 combines with a portion of a rear second surface 136 of head 104 that is opposite first surface 112 to provide a stabilizing feature for toothbrush 100. When a user puts toothbrush 100 down on a surface, such as a counter, stabilizing element 132 and second surface 136 work together to allow toothbrush 100 to rest in a stabilized position on the surface.

FIG. 2 illustrates a cross-sectional view of toothbrush 100 of FIG. 1. The cross-section shows the distribution of mass throughout the longitudinal axis of toothbrush 100. To shift the mass centroid toward tail end 130 of toothbrush 100, tail end 130 of handle 102 may be larger in volume and/or hold more mass. Alternatively or additionally, a head end or portion (e.g., head 104 and/or neck 103) of toothbrush 100 may be hollow or may comprise less dense material than a material of handle 102. In one or more arrangements, an object such as a weight 315 may be placed in or around a portion of handle 102 to shift the mass centroid of toothbrush 100. According to one or more aspects, the object may be secured to the tail end 130 or may be movable along a longitudinal axis of handle 102, as will be described in further detail below. A variety of methods, devices and systems may be used to modify the mass centroid of toothbrush 100.

FIGS. 3-4 illustrate toothbrush 300 with an adjustable mass centroid mechanism. A user may wish to adjust the mass centroid depending on the amount of counterweight they wish to have when brushing their teeth. Additionally, different users may hold a toothbrush at different points along the handle. For example, a user may hold the toothbrush closer to the toothbrush head while another user may hold the toothbrush further down toward the tail end. As such, the mass centroid may be adjusted to accommodate the various use scenarios and preferences.

Toothbrush 300 includes head 301 and handle 302. Handle 302 may include a handle shell 304 and a slider 305 for controlling a position of the mass centroid of toothbrush 300. Slider 305 may include a connecting portion 317 that extends into an interior cavity 320 of handle 302 enclosed by shell 304 through aperture 308. Connecting portion 317 of slider 305 may extend through aperture 308 to connect to weight 315 placed in cavity 320 of handle 302. The position of weight 315 along a longitudinal axis of handle 302 (and toothbrush 300) may correspond to the position of slider 305. By adjusting the position of weight 315, the location of the mass centroid may also be altered. Slider 305 may include a locking mechanism to prevent accidental movement of slider 305 and weight 315. For example, the locking mechanism may include adjustment control 310 that must be depressed in order to slide slider 305 along aperture 308.

The size and shape of aperture 308 may vary depending on the degree of adjustability a user desires. For example, aperture 308 may extend longitudinally a greater distance (e.g., over half the length of handle 302) if a higher degree of adjustability is desired. Further, a lateral width of aperture 308 may be defined based on the size and shape of the connecting portion. In one or more configurations, the lateral width of aperture 308 may be defined such that a frictional force between the walls of aperture 308 and the connecting portion is sufficient to prevent independent movement of slider 305 and the interior weight without an external force (e.g., a user engaging the slider control).

Weight 315 may be constructed of a variety of sizes and shapes depending on the size and shape of cavity 320 as well as the weight of a remainder of toothbrush 300. In one or more arrangements, at least a portion of weight 315 may contact handle shell 304 such that frictional force between handle shell 304 and the contacting portion of weight 315 prevents the weight 315 from moving from its own weight. Cavity 320 may be rectangular, circular or any other shape suitable for movement of an object located therein. Connecting portion 317, as discussed, extends through aperture 308 and connects to weight 315. Connecting portion 317 may be connected to weight 315 in a variety of manners and using a variety of means. For example, the connection may be made using magnetics, adhesives and/or mechanical devices such as interlocking hooks and/or screws. Alternatively, connecting portion 317 and weight 315 may be integrally formed through various manufacturing processes such as injection molding.

Weight 315 may comprise various types of materials such as metals and plastics. According to one or more aspects, weight 315 may be composed of a material that is denser than a remainder of toothbrush 300 (e.g., head 301 and handle shell 304). The density of the material may be relevant for conserving space while adding enough weight to sufficiently impact the location of the mass centroid.

According to one or more aspects, toothbrush 300 may further include one or more sensors such as pressure sensor 340, touch sensor 345 and/or gyroscopic sensor 350 for detecting various attributes of toothbrush 300. For example, a pressure sensor 340 may be placed in head 301 to determine a pressure being applied against a user's teeth. A touch sensor 345 may be used to determine a location of a user's grip while a gyroscopic sensor 350 may provide information relating to the orientation of the toothbrush. Further, information obtained from sensors 340, 345 and 350 may be used by processor 355 to perform one or more functions such as calculating an optimal location for a mass centroid.

FIGS. 5-6 illustrates toothbrush 500 having another mass centroid adjustment mechanism. Toothbrush 500 includes head 501 and handle 502. Tail end 505 of handle 502 may include a mass centroid control 507 that may be used to alter the location of the mass centroid of toothbrush 500. For example, control 507 may be rotatable along a longitudinal axis of toothbrush 500. Rotation of control 507 may cause the location of a weight 512 positioned in a cavity 515 of toothbrush 500 to change along a longitudinal axis of toothbrush 500. The change in location of weight 512 may be used to shift the position of the mass centroid to a desired point.

Adjustment control 507 may include a screw device 510 that extends into cavity 515 and connects to weight 512. Weight 512 may include a threaded aperture 517 for receiving screw device 510. Thus, as screw device 510 is rotated, weight 512 may be conveyed accordingly along the length of screw device 510, thus changing the location of weight 512 and the mass centroid. The length of screw device 510 and threaded aperture 517 may correspond to a desired range of motion of weight 512.

While the systems for adjusting a location of the mass centroid has been discussed herein with respect to two configurations, a variety of well-known mechanisms and systems for controlling the location of an object or device may be used. Various motors and other mechanical and electromechanical components may be used to provide such functionality. Still further, the aspects described herein may be used in conjunction with a manual toothbrush or an automatic/electric toothbrush.

Additionally or alternatively, a weight used to modify the mass centroid of a toothbrush may be either external or internal to the toothbrush or a combination of both. For example, a mass may be attached to an exterior portion of a toothbrush handle and moved along the exterior rather than within a cavity of the handle.

While the invention has been described with respect to specific examples including presently preferred modes of carrying out the invention, those skilled in the art will appreciate that there are numerous variations and permutations of the above described systems and techniques. Thus, the spirit and scope of the invention should be construed broadly as set forth in the appended claims.

What is claimed is:

1. An oral care instrument, comprising:
   a head;
   a handle comprising an object adjustable to a plurality of positions along a longitudinal axis of the handle, wherein the object is configured to modify a location of a mass centroid of the oral care instrument;
   one or more sensors operably coupled to a processor that provides feedback regarding an optimal location of the mass centroid; and
   wherein the handle is integrally formed with the head.

2. The handle of claim 1, wherein the object is adjustable using a slider control.

3. The handle of claim 1, wherein the object is located within a cavity of the handle.

4. The oral care implement of claim 2, wherein the object is located within a cavity of the handle, and wherein the slider control connects to the object via a connecting portion extending from an exterior portion of the handle into the cavity.

5. The oral care implement of claim 1, wherein the object comprises a first material of a first density and the head comprises a second material of a second density.

6. The oral care implement of claim 1, wherein the object is of a size such that an exterior surface of the object contacts an interior surface of the handle with a force sufficient to prevent the object from moving independently of an outside force.

7. The oral care implement of claim 5, wherein the first density is greater than the second density.

* * * * *